(12) United States Patent
Durschang et al.

(10) Patent No.: US 9,206,077 B2
(45) Date of Patent: Dec. 8, 2015

(54) DENTAL RESTORATION, METHOD FOR PRODUCTION THEREOF AND GLASS CERAMIC

(75) Inventors: Bernhard Durschang, Rottendorf (DE); Jörn Probst, Kürnach (DE); Norbert Thiel, Bad Säckingen (DE); Michael Gödiker, Bad Säckingen (DE); Markus Vollmann, Gelnhausen (DE); Udo Schusser, Alzenau (DE); Carsten Wiesner, Rockenberg (DE)

(73) Assignees: FRAUNHOFER-GESELLSCHAFT zur Förderung der angewandten Forschung e. V., München (DE); VITA ZAHNFABRIK H. RAUTER GMBH & CO. KG, Bad Sackingen (DE); DEGUDENT GMBH, Hanau (DE)

( * ) Notice: Subject to any disclaimer, the term of this patent is extended or adjusted under 35 U.S.C. 154(b) by 42 days.

(21) Appl. No.: 14/127,048

(22) PCT Filed: Jun. 18, 2012

(86) PCT No.: PCT/EP2012/061582
§ 371 (c)(1),
(2), (4) Date: Mar. 19, 2014

(87) PCT Pub. No.: WO2012/175450
PCT Pub. Date: Dec. 27, 2012

(65) Prior Publication Data
US 2014/0200129 A1 Jul. 17, 2014

Related U.S. Application Data

(60) Provisional application No. 61/499,815, filed on Jun. 22, 2011.

(30) Foreign Application Priority Data

Jun. 22, 2011 (EP) .................................... 11005102

(51) Int. Cl.
*C03C 10/04* (2006.01)
*C03C 10/00* (2006.01)
*C03B 32/02* (2006.01)
*C03C 3/097* (2006.01)
*A61K 6/00* (2006.01)
*A61K 6/02* (2006.01)
*A61K 6/027* (2006.01)

(52) U.S. Cl.
CPC ........... *C03C 10/0009* (2013.01); *A61K 6/0005* (2013.01); *A61K 6/0094* (2013.01); *A61K 6/024* (2013.01); *A61K 6/025* (2013.01); *A61K 6/0245* (2013.01); *A61K 6/0255* (2013.01); *A61K 6/0273* (2013.01); *C03B 32/02* (2013.01); *C03C 3/097* (2013.01); *C03C 10/0027* (2013.01)

(58) Field of Classification Search
CPC ............ C03C 10/0027; C03C 10/0009; C03C 10/0018
USPC ............................................................. 501/5
See application file for complete search history.

(56) References Cited

U.S. PATENT DOCUMENTS

| | | | |
|---|---|---|---|
| 2,684,911 A | 7/1954 | Stookey | |
| 3,238,085 A | 3/1966 | Hayami et al. | |
| 4,515,634 A | 5/1985 | Wu et al. | |
| 5,507,981 A | 4/1996 | Petticrew | |
| 5,698,482 A * | 12/1997 | Frank et al. | 501/10 |
| 5,925,180 A | 7/1999 | Frank et al. | |
| 6,420,288 B2 * | 7/2002 | Schweiger et al. | 501/7 |
| 7,166,548 B2 | 1/2007 | Apel et al. | |
| 7,452,836 B2 | 11/2008 | Apel et al. | |
| 7,867,930 B2 | 1/2011 | Apel et al. | |
| 7,867,931 B2 | 1/2011 | Apel et al. | |
| 7,867,933 B2 | 1/2011 | Apel et al. | |
| 7,871,948 B2 | 1/2011 | Apel et al. | |
| 7,993,137 B2 | 8/2011 | Apel et al. | |
| 8,162,664 B2 | 4/2012 | Apel et al. | |
| 8,536,078 B2 | 9/2013 | Ritzberger et al. | |
| 8,546,280 B2 | 10/2013 | Apel et al. | |
| 8,557,150 B2 | 10/2013 | Ritzberger et al. | |
| 8,759,237 B2 | 6/2014 | Ritzberger et al. | |
| 8,778,075 B2 | 7/2014 | Ritzberger et al. | |

(Continued)

FOREIGN PATENT DOCUMENTS

| | | |
|---|---|---|
| CA | 2213390 A1 | 3/1998 |
| CA | 2252660 A1 | 5/1999 |
| DE | 14 21 886 A1 | 6/1969 |
| DE | 24 51 121 A1 | 5/1975 |
| DE | 10 2004 013455 B3 | 9/2005 |
| DE | 10 2005 028637 A1 | 12/2006 |
| DE | 10 2007 011337 A1 | 9/2008 |
| EP | 0 536 572 A1 | 4/1993 |
| EP | 0 536 479 B1 | 9/1995 |
| EP | 0 690 031 A1 | 1/1996 |

(Continued)

OTHER PUBLICATIONS

Borom et al., "Strength and Microstructure in Lithium Disilicate Glass-Ceramics", *Journal of the American Ceramic Society*, vol. 58, No. 9-10, pp. 385-391 (1975).

(Continued)

*Primary Examiner* — Noah Wiese
(74) *Attorney, Agent, or Firm* — Leydig, Voit & Mayer, Ltd.

(57) ABSTRACT

The invention relates to glass ceramics, which show high strength, high translucency, high chemical stability and which are still mechanically processible. The invention further refers to a method for producing a dental restoration comprising such glass or glass ceramic as well as the dental restoration itself.

19 Claims, No Drawings

(56) References Cited

U.S. PATENT DOCUMENTS

| | | | |
|---|---|---|---|
| 2002/0010063 A1 | 1/2002 | Schweiger et al. | |
| 2005/0209082 A1 | 9/2005 | Apel et al. | |
| 2007/0042889 A1 | 2/2007 | Apel et al. | |
| 2009/0038344 A1* | 2/2009 | Apel et al. | ............ 65/61 |
| 2009/0038508 A1 | 2/2009 | Apel et al. | |
| 2009/0042713 A1 | 2/2009 | Apel et al. | |
| 2009/0042714 A1 | 2/2009 | Apel et al. | |
| 2010/0083706 A1 | 4/2010 | Castillo | |
| 2011/0030423 A1 | 2/2011 | Johannes et al. | |
| 2011/0059836 A1 | 3/2011 | Apel et al. | |
| 2011/0252831 A1 | 10/2011 | Apel et al. | |
| 2011/0256409 A1 | 10/2011 | Ritzberger et al. | |
| 2011/0257000 A1 | 10/2011 | Ritzberger et al. | |
| 2011/0259053 A1 | 10/2011 | Apel et al. | |
| 2012/0248642 A1 | 10/2012 | Ritzberger et al. | |
| 2012/0309607 A1 | 12/2012 | Durschang et al. | |
| 2013/0295523 A1 | 11/2013 | Durschang et al. | |
| 2013/0296156 A1 | 11/2013 | Apel et al. | |
| 2013/0323404 A1 | 12/2013 | Ritzberger et al. | |
| 2014/0000314 A1 | 1/2014 | Ritzberger et al. | |
| 2014/0200129 A1 | 7/2014 | Durschang et al. | |
| 2014/0249016 A1 | 9/2014 | Durschang et al. | |
| 2014/0335473 A1 | 11/2014 | Ritzberger et al. | |

FOREIGN PATENT DOCUMENTS

| | | |
|---|---|---|
| EP | 0 827 941 A1 | 3/1998 |
| EP | 0 916 625 A1 | 5/1999 |
| EP | 1 505 041 A1 | 2/2005 |
| EP | 1 688 397 A1 | 8/2006 |
| EP | 2 305 614 A2 | 4/2011 |
| EP | 2 377 831 A1 | 10/2011 |
| FR | 2 655 264 A | 6/1991 |
| JP | H08-040744 A | 2/1996 |
| JP | H10-101409 A | 4/1998 |
| JP | H11-314938 A | 11/1999 |
| JP | 2005-053776 A | 3/2005 |
| JP | 2006-219367 A | 8/2006 |
| JP | 2011-225441 A | 11/2011 |
| JP | 2013-515659 A | 5/2013 |
| SU | 908 355 A1 | 2/1982 |
| WO | WO 95/32678 A2 | 12/1995 |
| WO | WO 2009/126317 A1 | 10/2009 |
| WO | WO 2011/076422 A1 | 6/2011 |
| WO | WO 2012/059143 A1 | 5/2012 |
| WO | WO 2012/175615 A1 | 12/2012 |

OTHER PUBLICATIONS

De Oliveira et al., "Sintering and Crystallization of a Glass Powder in the $Li_2O$—$ZrO_2$—$SiO_2$ System," *Communications of the American Ceramic Society*, vol. 81, No. 3, pp. 777-780 (1998).

Montedo et al. "Low Thermal Expansion Sintered LZSA Glass-Ceramics," *American Ceramic Society Bulletin*, vol. 87. No. 7, pp. 34-40 (2008).

Stookey, "Chemical Machining of Photosensitive Glass", *Industrial and Engineering Chemistry*, 45, pp. 115-118 (1993).

Von Clausbruch et al., "Crystallization, Microstructure and Properties of Selected Glasses and Glass-Ceramics in the $SiO_2$—$Li_2O$—$ZnO$—$K_2O$—$P_2O_5$ System," *DGG Journal*, vol. 1, No. 1, pp. 41-49 (2002).

European Patent Office, International Search Report in International Application No. PCT/EP2012/061582 (Oct. 11, 2012).

* cited by examiner

DENTAL RESTORATION, METHOD FOR PRODUCTION THEREOF AND GLASS CERAMIC

CROSS-REFERENCE TO RELATED APPLICATIONS

This patent application is the U.S. national phase of International Application No. PCT/EP2012/061582, filed on Jun. 18, 2012, which claims the benefit of European Patent Application No. 11005102.6 and U.S. Provisional Application No. 61/499,815, both filed Jun. 22, 2011, the disclosures of which are incorporated by reference.

The invention relates to glass ceramics, which show high strength, high translucency, high chemical stability and which are still mechanically processible. The invention further refers to a method for producing a dental restoration comprising such glass or glass ceramic as well as the dental restoration itself.

In the lithium oxide-silicon dioxide system, lithium disilicate ($Li_2O.2\ SiO_2$ ($Li_2Si_2O_5$))-glass ceramics are well known from the literature and several patents are based on this glass ceramic system. In EP 0 536 479 B1, self-glazed lithium disilicate glass ceramic objects are thus described for the production of tableware and, in EP 0 536 572 B1, lithium disilicate glass ceramics which can be used by scattering a fine-particle coloured glass onto the surface thereof as cladding elements for building purposes.

A main focus of the publications about lithium disilicate glass ceramics resides in dental applications. The lithium disilicate system is very suitable here for the production of CAD/CAM-processible glass ceramics since the crystallisation is effected here via the lithium metasilicate phase (see S. D. Stookey: "Chemical Machining of Photosensitive Glass", Ind. Eng. Chem., 45, 115-118 (1993) and S. D. Stookey: "Photosensitively Opacifiable Glass" U.S. Pat. No. 2,684,911 (1954)).

These lithium metasilicate glass ceramics have such low strengths in this intermediate stage that they can be readily processed by means of CAD/CAM (M.-P. Borom, A. M. Turkalo, R. H. Doremus: "Strength and Microstructure in Lithium Disilicate Glass Ceramics", J. Am. Ceram. Soc., 58, No. 9-10, 385-391 (1975) and DE 24 51 121 A1.

Only by the subsequent conversion to lithium disilicate or the growing of lithium metasilicate crystals, in a second heat treatment, dental materials with high strength are achieved.

The heat treatment which is carried out in a dental laboratory or in the dental practice is a burden for a technician as well as for the patient with respect to time and costs. In particular, during the chairside method, inconvenient waiting times can occur.

In this method, an individually adapted crown/onlay/inlay is milled out of a glass ceramic block after the first crystallisation stage by means of CAD/CAM, in the dental practice this is subjected to the second crystallisation stage in a special oven and used directly in the first and only dentist's visit for the patient (DE 10 2005 028 637).

Such a heat treatment requires an oven and the corresponding acquisition and maintenance costs. Moreover, such a heat treatment can be the source for defects of the final product. Another drawback is the required time for such treatment which is between 30 and 60 minutes. For common CAD/CAM-systems, a maximum strength of 170 MPa is the limit. Thus, the machineable materials cannot be directly used for high quality applications. The machineability is not only dependent on the strength of the material, but also dependent on further properties, such as the hardness, the modulus of elasticity, the fracture toughness as well as the structure and microstructure of the glass ceramic. It has to be differentiated between intercrystalline and trans-crystalline fraction formes.

Starting herefrom, it was the object of the present invention to provide glass ceramics which have improved strength values and also improved translucence and chemical resistance.

This object is achieved by the method for producing a dental restoration described herein, and by the translucent and tooth coloured glass ceramic and the dental restoration that are also described herein, as well as the advantageous developments thereof.

Within the scope of the present invention, glass compositions were developed in the basic system $SiO_2$—$Li_2O$—$ZrO_2$, which have lithium metasilicate as only or as main crystal phase (>50%).

It was surprisingly found that the use of specific lithium metasilicate compositions together with specific heat treatments for its crystallisation can result in finally crystallized glass ceramics with a high strength which can be machined with CAD/CAM-techniques.

It was shown in addition that up to 20% by weight of $ZrO_2$ can be incorporated in the glass without the structure being significantly influenced. Contrary to all expectations, the $ZrO_2$ does not hereby crystallise as a separate crystal phase but remains completely or extensively in the amorphous residual glass phase. Because of the high proportion of $ZrO_2$, the mechanical and chemical resistances are hugely improved in this amorphous phase, which also leads to improved properties in the entire dental glass ceramic (crystal phase(s) and residual glass phase), such as for example final strength and acid solubility.

The method is also suitable for a two-stage production process from the initial glass, a partial crystallisation of the lithium metasilicate being effected in the first processing stage, which enables good CAD/CAM processing. In the second processing stage, an increase in the crystal phase proportion (primary lithium metasilicate) is effected, which leads to the high strength values. The most important cause of the surprisingly high strengths in the lithium metasilicate system is hereby ascribed to the high zirconium oxide proportion (>8 MA).

High translucence is ensured via the low crystallite size in the glass ceramics. In addition, good chemical stability is ensured by the high zirconium oxide proportion in the glass phase.

According to the present invention, a method for producing a dental restoration comprising a lithium silicate glass ceramic is provided having the following steps:

a) an amorphous glass is subjected to at least one heat treatment with temperatures from 450 to 1100° C. resulting in a translucent and tooth coloured glass ceramic with a strength of at least 250 MPa (measured according to DIN ISO 6872) and with the colour of tooth, wherein during the at least one heat treatment at least a partial crystallisation occurs due to the increased temperatures, and b) the glass ceramic is formed to a dental restoration for immediate dental application and with a strength of at least 200 MPa (measured according to DIN ISO 6872) by using a material removing process.

In the context of the present invention a translucent glass ceramic is a ceramic which has a transmission of light with a wavelength between 360 nm to 740 nm (measured according to DIN EN 410 with a spectrophotometer Minolta CM-3610d).

The tooth colour is determined in accordance with existing dental shade guides, e.g. Vita classical shade guide, Vita 3D master shade guide).

The stabilizer is preferably $ZrO_2$ and/or $HfO_2$. Preferably, the stabiliser is essentially present in an amorphous state.

There may be contained as additives components selected from the group consisting of nucleation agents, fluorescent agents, dyes, in particular glass-colouring oxides, coloured pigments and mixtures thereof, in the glass or in the glass ceramic.

The nucleating agents are preferably selected from the group consisting of phosphorous oxide, titanium oxide, tin oxide, mixtures thereof, and noble metals, preferably in an amount of 1 to 10 wt-%, more preferably 2 to 8 wt-% and most preferably 4 to 8 wt-%.

The fluorescent agents are preferably selected from the group consisting of oxides of bismuth, rare earth elements as neodymium, praseodymium, samarium, erbium, and europium, and mixtures thereof, preferably in an amount of 0.1 to 5 wt-%, more preferably 0.5 to 4 wt-% and most preferably 1 to 3 wt-%.

The glass colouring oxides are preferably selected from the group of oxides of iron, titanium, cerium, copper, chromium, cobalt, nickel, manganese, selenium, silver, indium, gold, vanadium, rare earth elements as neodymium, praseodymium, samarium, europium, terbium, dysprosium, holmium, erbium, yttrium, and mixtures thereof, preferably in an amount of 0.1 to 6 wt-%, more preferably 0.5 to 5 wt-% and most preferably 1 to 4 wt-%.

The coloured pigments can be doped spinels, which are comprised preferably in an amount of 0.1 to 6 wt-%, more preferably 0.5 to 5 wt-% and most preferably 1 to 4 wt-%.

Further additives are preferably selected from the group consisting of boron oxide, phosphorus oxide, fluorine, barium oxide, strontium oxide, magnesium oxide, zinc oxide, calcium oxide, yttrium oxide, titanium oxide, niobium oxide, tantalum oxide, lanthanum oxide and mixtures thereof, which are comprised preferably in an amount of 0.1 to 5 wt-%.

In a preferred embodiment, the amorphous glass has the following composition:
55 to 70 wt-% $SiO_2$,
10 to 25 wt-% $Li_2O$,
8 to 20 wt-% of a stabiliser selected from the group consisting of the oxides of Zr, Hf, Ge, La, Y, Ce, Ti, Zn or its mixtures,
0 to 10 wt-% $Al_2O_3$,
0 to 10 wt-% $K_2O$ and/or $Na_2O$, and
0 to 20 wt-% additives.

In a further preferred embodiment, the amorphous glass has the following composition:
55 to 70 wt-% $SiO_2$,
10 to 25 wt-% $Li_2O$,
8 to 20 wt-% of a stabiliser from a group selected of $ZrO_2$, $HfO_2$ or its mixtures,
0 to 10 wt-% $Al_2O_3$,
0 to 10 wt-% $K_2O$ and/or $Na_2O$, and
0 to 20 wt-% additives.

In a further preferred embodiment, the amorphous glass has the following composition:
55 to 64 wt-% $SiO_2$,
15 to 22 wt-% $Li_2O$,
8 to 20 wt-% of a stabiliser from a group selected of $ZrO_2$, $HfO_2$ or its mixtures,
0.1 to 8 wt-% $Al_2O_3$,
0 to 8 wt-% $K_2O$ and/or $Na_2O$, and
0 to 15 wt-% additives.

In a further preferred embodiment, the amorphous glass has the following composition:
55 to 64 wt-% $SiO_2$,
17 to 20 wt-% $Li_2O$,
8 to 20 wt-% of a stabiliser from a group selected of $ZrO_2$, $HfO_2$ or its mixtures,
0.1 to 5 wt-% $Al_2O_3$,
0.1 to 5 wt-% $K_2O$ and/or $Na_2O$,
2 to 8 wt-% $P_2O_5$, and
0 to 10 wt-% additives.

In a further preferred embodiment, the heat treatment is a single-stage treatment with a temperature from 600° C. to 950° C., preferably 780 to 900° C. It is another preferred embodiment that the heat treatment is a double-stage treatment with a first temperature from 600 to 800° C. and a second temperature from 780 to 900° C.

The lithium silicate glasses or glass ceramics according to the invention are used as dental material or as component of a dental material.

The material removing process is a subtractive process, preferably selected from the group consisting of milling, grinding, and laser ablation, preferably as a CAM process.

In a further preferred embodiment, the dental restoration is subjected to a finishing process before the dental application. Such a finishing process can be a polishing, a glazing, a sealing, a coating, and a veneering with a veneering ceramic or glaze.

The dental restoration is preferably an inlay, an onlay, a bridge, an abutment, a facing, a veneer, a facet, a crown, a partial crown, a framework or a coping.

According to the present invention, also a translucent and tooth coloured glass ceramic with a strength of at least 250 MPa (measured according to DIN ISO 6872) having the following composition is provided:
55 to 70 wt-% $SiO_2$,
10 to 25 wt-% $Li_2O$,
8 to 20 wt-% of a stabiliser from a group selected of Zr, Hf, Ge, La, Y, Ce, Ti, Zn or its mixtures,
0 to 10 wt-% $Al_2O_3$,
0 to 10 wt-% $K_2O$ and/or $Na_2O$, and
0 to 20 wt-% additives.

In a preferred embodiment, the glass ceramic has the following composition:
55 to 70 wt-% $SiO_2$,
10 to 25 wt-% $Li_2O$,
8 to 20 wt-% of a stabiliser from a group selected of $ZrO_2$, $HfO_2$ or its mixtures,
0 to 10 wt-% $Al_2O_3$,
0 to 10 wt-% $K_2O$ and/or $Na_2O$, and
0 to 20 wt-% additives.

Preferably, the glass ceramic has the following composition:
55 to 64 wt-% $SiO_2$,
15 to 22 wt-% $Li_2O$,
8 to 20 wt-% of a stabiliser from a group selected of $ZrO_2$, $HfO_2$ or its mixtures,
0.1 to 8 wt-% $Al_2O_3$,
0 to 8 wt-% $K_2O$ and/or $Na_2O$, and
0 to 15 wt-% additives.

In a further preferred embodiment, the glass ceramic has the following composition:
55 to 64 wt-% $SiO_2$,
17 to 20 wt-% $Li_2O$,
8 to 20 wt-% of a stabiliser from a group selected of $ZrO_2$, $HfO_2$ or its mixtures, 0.1 to 5 wt-% $Al_2O_3$,
0.1 to 5 wt-% $K_2O$ and/or $Na_2O$,
2 to 8 wt-% $P_2O_5$, and
0 to 10 wt-% additives.

The glass ceramic has preferably a dimensional stability which allows the machining of the glass ceramic with a material removing process.

According to the present invention, furthermore, a dental restoration is provided which is producible by the above described method.

It is preferred that the dental restoration has a degree of crystallization of at least 5%, preferably at least 50%.

It is further preferred that the dental restoration has a strength of at least 200 MPa, preferably at least 300 MPa.

The dental restoration can have a finishing. Such a finishing is preferably a polishing, a glazing, a sealing, a coating, and a veneering with a veneering ceramic or glaze. Such a finished dental restoration has preferably a strength of at least 250 MPa, preferably of at least 300 MPa.

The dental restorations with the following compositions are further aspects of the present invention:

| Composition 1 | |
|---|---|
| $SiO_2$ | 50 to 75 wt-% |
| $Li_2O$ | 10 to 25 wt-% |
| $ZrO_2$ | 8 to 20 wt-% |
| $Al_2O_3$ | 0 to 8 wt-% |
| $K_2O$ | 0 to 8 wt-% |
| additives | 0 to 15 wt-% |

| Composition 5 | |
|---|---|
| $SiO_2$ | 50 to 75 wt-% |
| $Li_2O$ | 17 to 20 wt-% |
| $ZrO_2$ | 8 to 20 wt-% |
| $Al_2O_3$ | 0 to 8 wt-% |
| $K_2O$ | 0 to 8 wt-% |
| additives | 0 to 15 wt-% |

| Composition 2 | |
|---|---|
| $SiO_2$ | 50 to 64 wt-% |
| $Li_2O$ | 10 to 25 wt-% |
| $ZrO_2$ | 8 to 20 wt-% |
| $Al_2O_3$ | 0 to 8 wt-% |
| $K_2O$ | 0 to 8 wt-% |
| additives | 0 to 15 wt-% |

| Composition 6 | |
|---|---|
| $SiO_2$ | 50 to 75 wt-% |
| $Li_2O$ | 10 to 25 wt-% |
| $ZrO_2$ | 8 to 20 wt-% |
| $Al_2O_3$ | 0 to 8 wt-% |
| $K_2O$ | 0 to 8 wt-% |
| additives | 0 to 15 wt-% |

| Composition 3 | |
|---|---|
| $SiO_2$ | 55 to 60 wt-% |
| $Li_2O$ | 10 to 25 wt-% |
| $ZrO_2$ | 8 to 20 wt-% |
| $Al_2O_3$ | 0 to 8 wt-% |
| $K_2O$ | 0 to 8 wt-% |
| additives | 0 to 15 wt-% |

| Composition 7 | |
|---|---|
| $SiO_2$ | 50 to 75 wt-% |
| $Li_2O$ | 10 to 25 wt-% |
| $ZrO_2$ | 10 to 15 wt-% |
| $Al_2O_3$ | 0 to 8 wt-% |
| $K_2O$ | 0 to 8 wt-% |
| additives | 0 to 15 wt-% |

| Composition 4 | |
|---|---|
| $SiO_2$ | 50 to 75 wt-% |
| $Li_2O$ | 15 to 22 wt-% |
| $ZrO_2$ | 8 to 20 wt-% |
| $Al_2O_3$ | 0 to 8 wt-% |
| $K_2O$ | 0 to 8 wt-% |
| additives | 0 to 15 wt-% |

| Composition 8 | |
|---|---|
| $SiO_2$ | 50 to 75 wt-% |
| $Li_2O$ | 10 to 25 wt-% |
| $ZrO_2$ | 8 to 20 wt-% |
| $Al_2O_3$ | 0.1 to 5 wt-% |
| $K_2O$ | 0 to 8 wt-% |
| additives | 0 to 15 wt-% |

| Composition 9 | |
|---|---|
| $SiO_2$ | 50 to 75 wt-% |
| $Li_2O$ | 10 to 25 wt-% |
| $ZrO_2$ | 8 to 20 wt-% |
| $Al_2O_3$ | 1 to 3 wt-% |
| $K_2O$ | 0 to 8 wt-% |
| additives | 0 to 15 wt-% |

| Composition 15 | |
|---|---|
| $SiO_2$ | 50 to 75 wt-% |
| $Li_2O$ | 10 to 25 wt-% |
| $ZrO_2$ | 8 to 20 wt-% |
| $P_2O_5$ | 1 to 10 wt-% |
| $Al_2O_3$ | 0 to 8 wt-% |
| $K_2O$ | 0 to 8 wt-% |
| additives | 0 to 5 wt-% |

| Composition 10 | |
|---|---|
| $SiO_2$ | 50 to 75 wt-% |
| $Li_2O$ | 10 to 25 wt-% |

Composition 10

| | |
|---|---|
| $ZrO_2$ | 8 to 20 wt-% |
| $Al_2O_3$ | 0 to 8 wt-% |
| $K_2O$ | 0.1 to 5 wt-% |
| additives | 0 to 15 wt-% |

Composition 16

| | |
|---|---|
| $SiO_2$ | 50 to 75 wt-% |
| $Li_2O$ | 10 to 25 wt-% |
| $ZrO_2$ | 8 to 20 wt-% |
| $P_2O_5$ | 2 to 8 wt-% |
| $Al_2O_3$ | 0 to 8 wt-% |
| $K_2O$ | 0 to 8 wt-% |
| additives | 0 to 7 wt-% |

Composition 11

| | |
|---|---|
| $SiO_2$ | 50 to 75 wt-% |
| $Li_2O$ | 10 to 25 wt-% |
| $ZrO_2$ | 8 to 20 wt-% |
| $Al_2O_3$ | 0 to 8 wt-% |
| $K_2O$ | 1 to 3 wt-% |
| additives | 0 to 15 wt-% |

Composition 17

| | |
|---|---|
| $SiO_2$ | 50 to 75 wt-% |
| $Li_2O$ | 10 to 25 wt-% |
| $ZrO_2$ | 8 to 20 wt-% |
| $P_2O_5$ | 4 to 6 wt-% |
| $Al_2O_3$ | 0 to 8 wt-% |
| $K_2O$ | 0 to 8 wt-% |
| additives | 0 to 9 wt-% |

Composition 12

| | |
|---|---|
| $SiO_2$ | 50 to 75 wt-% |
| $Li_2O$ | 10 to 25 wt-% |
| $ZrO_2$ | 8 to 20 wt-% |
| $Al_2O_3$ | 0 to 8 wt-% |
| $K_2O$ | 0 to 8 wt-% |
| additives | 1 to 10 wt-% |

Composition 18

| | |
|---|---|
| $SiO_2$ | 55 to 64 wt-% |
| $Li_2O$ | 10 to 25 wt-% |
| $ZrO_2$ | 8 to 20 wt-% |
| $P_2O_5$ | 1 to 10 wt-% |
| $Al_2O_3$ | 0 to 8 wt-% |
| $K_2O$ | 0 to 8 wt-% |
| additives | 0 to 5 wt-% |

Composition 13

| | |
|---|---|
| $SiO_2$ | 50 to 75 wt-% |
| $Li_2O$ | 10 to 25 wt-% |
| $ZrO_2$ | 8 to 20 wt-% |
| $Al_2O_3$ | 0 to 8 wt-% |
| $K_2O$ | 0 to 8 wt-% |
| additives | 2 to 8 wt-% |

Composition 19

| | |
|---|---|
| $SiO_2$ | 55 to 64 wt-% |
| $Li_2O$ | 15 to 22 wt-% |
| $ZrO_2$ | 8 to 20 wt-% |
| $P_2O_5$ | 1 to 10 wt-% |
| $Al_2O_3$ | 0 to 8 wt-% |
| $K_2O$ | 0 to 8 wt-% |
| additives | 0 to 5 wt-% |

Composition 14

| | |
|---|---|
| $SiO_2$ | 50 to 75 wt-% |
| $Li_2O$ | 10 to 25 wt-% |
| $ZrO_2$ | 8 to 20 wt-% |
| $Al_2O_3$ | 0 to 8 wt-% |
| $K_2O$ | 0 to 8 wt-% |
| additives | 4 to 6 wt-% |

Composition 20

| | |
|---|---|
| $SiO_2$ | 55 to 64 wt-% |
| $Li_2O$ | 17 to 20 wt-% |
| $ZrO_2$ | 8 to 20 wt-% |
| $P_2O_5$ | 1 to 10 wt-% |
| $Al_2O_3$ | 0 to 8 wt-% |
| $K_2O$ | 0 to 8 wt-% |
| additives | 0 to 5 wt-% |

Composition 24

| | |
|---|---|
| $SiO_2$ | 55 to 64 wt-% |
| $Li_2O$ | 10 to 25 wt-% |
| $ZrO_2$ | 8 to 20 wt-% |
| $P_2O_5$ | 1 to 10 wt-% |
| $Al_2O_3$ | 1 to 3 wt-% |
| $K_2O$ | 0 to 8 wt-% |
| additives | 0 to 5 wt-% |

Composition 25

| | |
|---|---|
| $SiO_2$ | 55 to 64 wt-% |
| $Li_2O$ | 10 to 25 wt-% |
| $ZrO_2$ | 8 to 20 wt-% |
| $P_2O_5$ | 1 to 10 wt-% |
| $Al_2O_3$ | 0 to 8 wt-% |
| $K_2O$ | 0.1 to 5 wt-% |
| additives | 0 to 5 wt-% |

Composition 13

| | |
|---|---|
| $SiO_2$ | 50 to 75 wt-% |
| $Li_2O$ | 10 to 25 wt-% |
| $ZrO_2$ | 8 to 20 wt-% |

Composition 21

| | |
|---|---|
| $SiO_2$ | 55 to 64 wt-% |
| $Li_2O$ | 10 to 25 wt-% |
| $ZrO_2$ | 8 to 20 wt-% |

-continued

| Composition 21 | |
|---|---|
| $P_2O_5$ | 1 to 10 wt-% |
| $Al_2O_3$ | 0 to 8 wt-% |
| $K_2O$ | 0 to 8 wt-% |
| additives | 0 to 5 wt-% |

| Composition 26 | |
|---|---|
| $SiO_2$ | 55 to 64 wt-% |
| $Li_2O$ | 10 to 25 wt-% |
| $ZrO_2$ | 8 to 20 wt-% |
| $P_2O_5$ | 1 to 10 wt-% |
| $Al_2O_3$ | 0 to 8 wt-% |
| $K_2O$ | 1 to 3 wt-% |
| additives | 0 to 5 wt-% |

| Composition 22 | |
|---|---|
| $SiO_2$ | 55 to 64 wt-% |
| $Li_2O$ | 10 to 25 wt-% |
| $ZrO_2$ | 8 to 15 wt-% |
| $P_2O_5$ | 1 to 10 wt-% |
| $Al_2O_3$ | 0 to 8 wt-% |
| $K_2O$ | 0 to 8 wt-% |
| additives | 0 to 5 wt-% |

| Composition 23 | |
|---|---|
| $SiO_2$ | 55 to 64 wt-% |
| $Li_2O$ | 10 to 25 wt-% |
| $ZrO_2$ | 5 to 30 wt-% |
| $P_2O_5$ | 1 to 10 wt-% |
| $Al_2O_3$ | 0.1 to 5 wt-% |
| $K_2O$ | 0 to 8 wt-% |
| additives | 0 to 5 wt-% |

The subject according to the application is intended to be explained in more detail with reference to the subsequent examples without restricting said subject to these variants.

EXAMPLE 1

In Table 1, a fixed compositions given by way of example for different stabilizer is mentioned, from which high stabilizer-containing metasilicate glass ceramics can be produced for the dental field.

TABLE 1

| | in % by weight |
|---|---|
| $SiO_2$ | 60.0 |
| $Li_2O$ | 19.0 |
| $P_2O_5$ | 6.0 |
| $Al_2O_3$ | 2.0 |
| $K_2O$ | 2.0 |
| $CeO_2$ | 1.0 |
| Stabilizer SX* | 10.0 |

*SX represent compositions of stabilizers S1 to S5 (s. table 2)

Table 2 shows stabilizers used by way of example for dental applications with the composition of table 1.

TABLE 2

| | Stabilizers SX |
|---|---|
| S1 | Zirconium oxide: 10% |
| S2 | Germanium oxide: 10% |
| S3 | Lanthanum oxide: 10% |
| S4 | Yttrium oxide: 10% |
| S5 | Zirconium oxide: 6% |
| | Titanium oxide: 4% |

The glasses were melted at 1,500° C. and poured into metal moulds to form blocks. The blocks were stressrelieved in the oven at 560° C. and cooled down slowly. For the various characterisation processes, the glass blocks were divided up and subjected to a first crystallisation treatment. For this purpose, the glasses were stored for 10 to 120 minutes at 600° C. to 750° C. As a result of this, glass ceramics with strength values of 150 MPa to 220 MPa were produced. Exclusively lithium metasilicate was hereby established as crystal phase. In this state, processing by means of CAD/CAM methods is possible very readily.

In Table 3, compositions which are given by way of example are mentioned, from which high zirconium oxide-containing metasilicate glass ceramics can be produced for the dental field.

TABLE 3

| | G1* | G2* | G3* | G4* | G5* | G6* |
|---|---|---|---|---|---|---|
| $SiO_2$ | 63.5 | 63.5 | 59.0 | 59.0 | 63.5 | 63.5 |
| $Li_2O$ | 12.9 | 13.9 | 18.0 | 19.0 | 12.9 | 12.9 |
| $ZrO_2$ | 10.0 | 9.0 | 12.0 | 12.0 | 12.3 | 11.0 |
| $Al_2O_3$ | 4.7 | 5.1 | 4.5 | 4.5 | 3.9 | 4.4 |
| $P_2O_5$ | 4.5 | 4.5 | 3.5 | 3.5 | 3.7 | 4.2 |
| $K_2O$ | 4.4 | 4.0 | 3.0 | 2.0 | 3.6 | 4.0 |

*(Data in % by weight)

The glasses were melted at 1,500° C. and poured into metal moulds to form blocks. The blocks were stressrelieved in the oven at 560° C. and cooled down slowly. For the various characterisation processes, the glass blocks were divided up and subjected to a first crystallisation treatment. For this purpose, the glasses were stored for 10 to 120 minutes at 600° C. to 750° C. As a result of this, glass ceramics with strength values of 150 MPa to 220 MPa were produced. Exclusively lithium metasilicate was hereby established as crystal phase. In this state, processing by means of CAD/CAM methods is possible very readily.

EXAMPLE 2

A glass melt with a composition of 60 wt % $SiO_2$, 19 wt % $LiO_2$, 10 wt % $ZrO_2$, 6 wt % $P_2O_5$, 2 wt % $Al_2O_3$, 2 wt % $K_2O$ and 2 wt % $CeO_2$ is cast into a block form. This block is completely crystallized by a two-step firing process. The heat treatment is carried out at 620° C. and 850° C. After this procedure a block holder (e.g. metal attachment) is glued to the block to fix it in a CAM machine.

For this application a dental milling machine (Sirona in Lab MCXL) is used. For a first test the preinstalled parameters for presintered IPS e.max CAD (Software version 3.85) were chosen. A designed anterior crown was milled by using the typical diamond tools. The expected milling time was 17 minutes; the real milling time took 28 min. The chosen burs and the resulting crown showed no problems.

In a second test an identical crown was milled in the same machine by selecting the preinstalled parameters for VITA In-Ceram Spinell. The milling process took also ca. 10 minutes longer than the time calculated. The crown and grinders showed no defects.

After milling the surface of the crown can be optimized by hand. A typical procedure for a dental technician or dentist can be e.g. polishing, glazing, staining and veneering. Bendbars machined after final crystallizing and treated with a glaze showed fracture values of 370 MPa (3-point-bending strength test conform to DIN EN ISO 6872)

Comparative Test

The commercially available product IPS e.max CAD (Ivoclar-Vivadent, color LT A2) was tested in a comparative way. For this reason the blocks were additionally heat treated at 850° C. The holder, which was removed before final heat treatment, was attached again by gluing.

Then the same crown design was loaded again and the parameters for (normally only partially crystallized) IPS e.max CAD were selected. The complete milling process took ca. 90 minutes instead of the calculated minutes. The process had to be restarted four times because four diamond grinders broke during the process. This shows that it is not possible to machine finally crystallized IPS e.max CAD crowns in a commercially successful way.

The invention claimed is:

1. A method for producing a dental restoration comprising a lithium silicate glass ceramic, wherein
   a) an amorphous glass having the following composition:
   55 to 70 wt-% $SiO_2$,
   15 to 22 wt-% $Li_2O$,
   8 to 20 wt-% of a stabiliser selected from the group consisting of $ZrO_2$, $HfO_2$, and mixtures thereof,
   0 to 10 wt-% $Al_2O_3$,
   0 to 10 wt-% $K_2O$ and/or $Na_2O$,
   0 to 8 wt-% $P_2O_5$, and
   0 to 20 wt-% additives,
   is subjected to at least one heat treatment with temperatures from 450 to 1100° C. resulting in a translucent and tooth coloured and glass ceramic with a strength of at least 250 MPa (measured according to DIN ISO 6872) and with the colour of tooth, wherein during the at least one heat treatment at least a partial crystallisation occurs due to the increased temperatures, and
   b) the glass ceramic is formed into a dental restoration for immediate dental application and with a strength of at least 200 MPa (measured according to DIN ISO 6872) by a material removing process.

2. The method of claim 1, wherein the heat treatment is a single-stage treatment with a temperature from 600° C. to 950° C. or the heat treatment is a double-stage treatment with a first temperature from 600 to 800° C. and a second temperature from 780 to 900° C.

3. The method of claim 1, wherein the additives are selected from the group consisting of nucleating agents, fluorescent agents, dyes, glass colouring oxides, coloured pigments, and mixtures thereof.

4. The method of claim 3, wherein the nucleating agents are selected from the group consisting of phosphorous oxide, titanium oxide, tin oxide, mixtures thereof, and noble metals.

5. The method of claim 3, wherein the fluorescent agents are selected from oxides of bismuth, rare earth elements, neodymium, praseodymium, samarium, europium, terbium, dysprosium, holmium, erbium, and mixtures thereof.

6. The method of claim 3, wherein the glass colouring oxides are selected from oxides of iron, titanium, cerium, copper, chromium, cobalt, nickel, manganese, selenium, silver, indium, gold, vanadium, rare earth elements, neodymium, praseodymium, samarium, europium, terbium, dysprosium, holmium, erbium, yttrium, and mixtures thereof, and wherein the coloured pigments are doped spinels.

7. The method of claim 1, wherein the additives are selected from boron oxide, fluorine, barium oxide, strontium oxide, magnesium oxide, zinc oxide, calcium oxide, yttrium oxide, titanium oxide, niobium oxide, tantalum oxide, lanthanum oxide and mixtures thereof.

8. The method of claim 1, wherein the material removing process is a subtractive process selected from milling, grinding, and laser ablation.

9. The method of claim 1, wherein before the dental application, the dental restoration is subjected to a finishing process selected from polishing, glazing, sealing, coating, and veneering with a veneering ceramic or glaze.

10. A translucent and tooth coloured glass ceramic with a strength of at least 250 MPa (measured according to DIN ISO 6872) having the following composition:
    55 to 70 wt-% $SiO_2$,
    15 to 22 wt-% $Li_2O$,
    8 to 20 wt-% of a stabiliser selected from $ZrO_2$, $HfO_2$, and mixtures thereof,
    0 to 10 wt-% $Al_2O_3$,
    0 to 10 wt-% $K_2O$ and/or $Na_2O$, and
    0 to 20 wt-% additives.

11. The translucent and tooth coloured glass ceramic of claim 10, which has the following composition:
    55 to 64 wt-% $SiO_2$,
    15 to 22 wt-% of $Li_2O$,
    8 to 20 wt-% of a stabiliser selected from $ZrO_2$, $HfO_2$ and its mixtures,
    0 to 10 wt-% of $Al_2O_3$,
    0 to 10 wt-% of $K_2O$ and/or $Na_2O$,
    0 to 8 wt-% $P_2O_5$, and
    0 to 20 wt-% of additives.

12. The translucent and tooth coloured glass ceramic of claim 10, wherein the translucent and tooth coloured glass ceramic has a dimensional stability which allows the machining of the translucent and tooth coloured glass ceramic with a material removing process.

13. A dental restoration produced by the method of claim 1.

14. The dental restoration of claim 13, wherein the dental restoration has a degree of crystallization of at least 5% and/or the dental restoration has a strength of at least 200 MPa (measured according to DIN ISO 6872).

15. The dental restoration of claim 13, wherein the dental restoration has a finishing and the finished dental restoration has a strength of at least 250 MPa (measured according to DIN ISO 6872).

16. The method of claim 1, wherein the amorphous glass has the following composition:
    55 to 64 wt-% $SiO_2$,
    15 to 22 wt-% $Li_2O$,
    8 to 20 wt-% of a stabiliser selected from $ZrO_2$, $HfO_2$ and mixtures thereof,
    0.1 to 8 wt-% $Al_2O_3$,
    0.1 to 8 wt-% $K_2O$ and/or $Na_2O$,
    2 to 8 wt-% $P_2O_5$, and
    0 to 10 wt-% additives.

17. The method of claim 4, wherein the nucleating agents are present in an amount of 1 to 10 wt-% of the dental restoration.

18. The method of claim 5, wherein the fluorescent agents are present in an amount of 0.1 to 5 wt-% of the dental restoration.

19. The method of claim 6, wherein the glass colouring oxides are present in an amount of 0.1 to 6 wt-% of the dental restoration.

* * * * *